United States Patent
Kohlrausch

(10) Patent No.: US 9,029,363 B2
(45) Date of Patent: *May 12, 2015

(54) TELMISARTAN SODIUM SALT PHARMACEUTICAL FORMULATION

(75) Inventor: Anja Kohlrausch, Biberach (DE)

(73) Assignee: Boehringer Ingelheim International GmbH, Ingelheim (DE)

(*) Notice: Subject to any disclaimer, the term of this patent is extended or adjusted under 35 U.S.C. 154(b) by 2072 days.

This patent is subject to a terminal disclaimer.

(21) Appl. No.: 10/825,580

(22) Filed: Apr. 15, 2004

(65) Prior Publication Data

US 2005/0004107 A1 Jan. 6, 2005

Related U.S. Application Data

(60) Provisional application No. 60/471,675, filed on May 19, 2003.

(30) Foreign Application Priority Data

Apr. 30, 2003 (DE) .................................. 103 19 450

(51) Int. Cl.
- *C07D 403/04* (2006.01)
- *A61K 9/20* (2006.01)
- *A61K 31/39* (2006.01)
- *A61K 31/4184* (2006.01)

(52) U.S. Cl.
CPC .............. *A61K 9/2027* (2013.01); *A61K 9/2059* (2013.01); *C07D 403/04* (2013.01); *A61K 9/2018* (2013.01); *A61K 31/39* (2013.01); *A61K 9/2054* (2013.01); *A61K 31/4184* (2013.01)

(58) Field of Classification Search
USPC ......................................................... 514/183
See application file for complete search history.

(56) References Cited

U.S. PATENT DOCUMENTS

| | | | |
|---|---|---|---|
| 5,591,762 A | 1/1997 | Hauel | |
| 6,071,939 A | 6/2000 | Gaviraghi | |
| 6,358,986 B1 | 3/2002 | Schneider | |
| 6,410,742 B1 | 6/2002 | Schneider | |
| 6,737,432 B2 * | 5/2004 | Donsbach et al. ........... | 514/394 |
| 2002/0094997 A1 | 7/2002 | Schneider et al. | |
| 2003/0130331 A1 | 7/2003 | Donsbach | |
| 2003/0139608 A1 | 7/2003 | Belzer | |
| 2003/0171415 A1 | 9/2003 | Boehm | |
| 2004/0110813 A1 * | 6/2004 | Nakatani et al. ............. | 514/394 |
| 2004/0242891 A1 | 12/2004 | Campbell et al. | |
| 2004/0259925 A1 * | 12/2004 | Riedel et al. ................. | 514/381 |

FOREIGN PATENT DOCUMENTS

| | | |
|---|---|---|
| CA | 2060624 A1 | 8/1992 |
| CA | 2060624 | 12/1999 |
| EP | 0502 314 A1 | 9/1992 |
| EP | 502314 A1 | 9/1992 |
| RU | 2053229 C1 | 1/1996 |
| WO | 0105674 A2 | 3/2001 |
| WO | 0243807 A2 | 6/2002 |
| WO | 03037846 A1 | 5/2003 |
| WO | 03037876 A1 | 5/2003 |
| WO | WO 03/037846 A1 | 5/2003 |
| WO | 03059327 A1 | 7/2003 |

OTHER PUBLICATIONS

Lancourciere Y, Martin K, American Journal of Therapeutics, Mar.-Apr. 2002, 9(2), 111-117.*
Dinnebier et al., Structural Characterization of three crystalline modifications of telmisartan by single crystal and high-resolution x-ray powder diffraction, 2000, Journal of Pharmaceutical Sciences, vol. 89, No. 11, pp. 1465-1479.*
Vippagunta et al., Crystalline Solids, 2001, Advanced Drug Delivery Reviews, vol. 48, pp. 3-26.*
Sharpe et al., Telmisartan: A Review of its Use in Hypertension, 2001, Drugs, vol. 61, No. 10, pp. 1501-1529.*
Disclosure of Prior Art Sale Under § 102(b).
Freytag, F., et al—Telmisartan, Hypertension Experience in a Randomized European Study . . . pp. 108-123, 2001.
Lacourciere, Y. A new Fixed-dose Combination for Added Blood Pressure Control; pp. 366-379, 2002.
Neutel, J.M., et al; Long Term Efficacy and Tolerability of Telmisartan as Monotherapy . . . gs 302-309, 2002.
Richter A., et al; Mild to Moderate uncomplicated hypertension ; Further Analysis of a cost effectiveness study of live drugs. pp. 61-69, 2001.
Scarpa, William J., Micardis/HCT(telmisartan/hydrochlorothiazide) New Therapy update; Journal of Clinical Hypertension vol. 3, No. 4, Jul./Aug. 2001.
Wienen, W., et al; Effects of Telmisartan, Hydrochlorothizaide and their combination on blood pressure and renal excretory parametersin spontaneously hypertensive rats, 2001.
International Search Report for PCT/EP04/004425 mailed Aug. 16, 2004.

* cited by examiner

Primary Examiner — James D Anderson
Assistant Examiner — Meghan Finn
(74) *Attorney, Agent, or Firm* — Michael P. Morris; Timothy X. Witkowski; Usha R. Patel

(57) ABSTRACT

The invention relates to a pharmaceutical formulation of the crystalline sodium salt of 4'-[2-n-propyl-4-methyl-6-(1-methylbenzimidazol-2-yl)benzimidazol-1-ylmethyl]biphenyl-2-carboxylic acid (telmisartan), and to processes for the preparation thereof.

14 Claims, No Drawings

US 9,029,363 B2

TELMISARTAN SODIUM SALT PHARMACEUTICAL FORMULATION

RELATED APPLICATIONS

This application claims benefit of U.S. Ser. No. 60/471,675, filed May 19, 2003, and claims priority to German Application No. 103 19 450.9, filed Apr. 30, 2003, each of which is hereby incorporated by reference in its entirety.

FIELD OF THE INVENTION

The invention relates to a pharmaceutical formulation of the crystalline sodium salt of 4'-[2-n-propyl-4-methyl-6-(1-methylbenzimidazol-2-yl)benzimidazol-1-ylmethyl]biphenyl-2-carboxylic acid (telmisartan), as well as processes for the preparation thereof.

BACKGROUND OF THE INVENTION

The compound telmisartan is known from European Patent EP 502 314 B1 (corresponding to U.S. Pat. No. 5,591,762, which is hereby incorporated by reference) and has the following chemical structure:

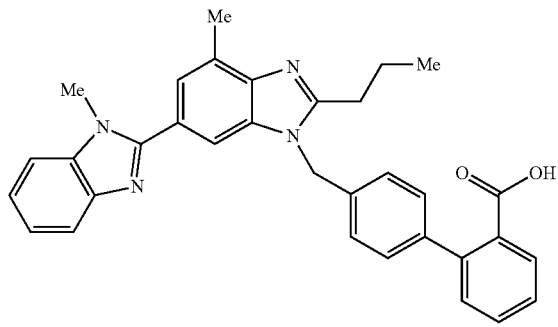 [SMILES: CCCc1nc2c(C)cc(-c3nc4ccccc4n3C)cc2n1Cc1ccc(-c2ccccc2C(=O)O)cc1]

Telmisartan, and the physiologically acceptable salts thereof, have valuable pharmacological properties. Telmisartan is an angiotensin antagonist, particularly an angiotensin II antagonist which, by virtue of its pharmacological properties, may be used, for example, to treat hypertension and cardiac insufficiency, to treat ischemic peripheral circulatory disorders and myocardial ischaemia (angina), to prevent the progression of cardiac insufficiency after myocardial infarct, and to treat diabetic neuropathy, glaucoma, gastrointestinal diseases and bladder diseases. Other possible therapeutic applications can be found in EP 502 314 B1 and WO 02/15891, the contents of which are hereby referred to.

Hydrochlorothiazide (HCTZ) is a thiazide diuretic which is taken orally to treat edema and high blood pressure. The chemical name of HCTZ is 6-chloro-3,4-dihydro-2H-1,2,4-benzothiadiazin-7-sulfonamide-1,1-dioxide and the compound has the following structural formula:

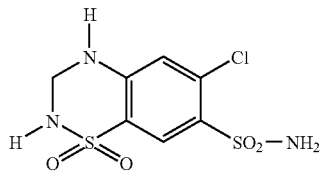

Telmisartan is commercially obtainable under the trademark MICARDIS®, while a combination of telmisartan with hydrochlorothiazide (HCTZ) is commercially obtainable under the trademark MICARDIS® HCT (MICARDIS PLUS in Europe). Starting from the free acid of telmisartan, these formulations are produced by a complex spray drying process. Because of the limited solubility of the free acid, less complex methods of preparing an alternative preparation are difficult to achieve.

The aim of the present invention is to provide telmisartan in a form which enables a formulation of this active substance to be prepared in a less complex form. It has to be borne in mind that generally the production of a composition containing a pharmaceutically active substance is dependent on various parameters which are linked to the nature of the active ingredient itself. Without being tied thereto, examples of these parameters are the stability of effect of the starting material under different environmental conditions, the stability during the manufacture of the pharmaceutical formulation, and the stability in the final compositions of the pharmaceutical preparation. The pharmaceutically active substance used to prepare the abovementioned pharmaceutical composition should be as pure as possible. At the same time, its stability on long-term storage must be guaranteed under various environmental conditions. This is absolutely essential, in order to prevent pharmaceutical compositions being used which contain, in addition to the active substance proper, breakdown products thereof. In such a case, the actual content of active substance present in a preparation produced therefrom may be less than the specified amount.

Another aspect which is important in the production of solid preparations is that the active substance should have the most stable possible crystalline morphology for the pharmaceutical quality of a medicinal formulation. If this is not the case, the morphology of the active substance may change in certain circumstances under the conditions of manufacture of the preparation. Such a change may in turn affect the reproducibility of the manufacturing process and thus lead to final formulations which do not meet the high quality requirements imposed on pharmaceutical formulations. To this extent it should generally be borne in mind that any change to the solid state of a pharmaceutical composition which can improve its physical and chemical stability gives a significant advantage over less stable forms of the same drug.

The object of the invention is thus to provide a new pharmaceutical composition containing a stable form of telmisartan which complies with the abovementioned stringent requirements imposed on a pharmaceutically active substance.

DETAILED DESCRIPTION OF THE INVENTION

Surprisingly, it has been found that telmisartan can be obtained in crystalline form, in the form of its sodium salt of formula 1

1

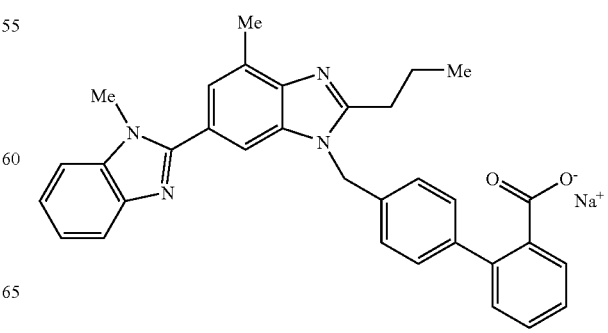

By a suitable choice of manufacturing conditions, the polymorphic form of the crystalline sodium salt which meets the abovementioned requirements can be selectively obtained.

This crystalline form of the sodium salt of telmisartan is characterized by a melting point of T=245±5° C. (determined by Differential Scanning Calorimetry (DSC); heating rate: 10 K/min). The following Table 1 summarizes the data obtained in a spectroscopic analysis of the salt:

TABLE 1

| 2Θ [°] | d [Å] | rel. intensity [%] |
|---|---|---|
| 3.54 | 24.96 | 7 |
| 4.21 | 20.95 | 100 |
| 4.45 | 19.83 | 20 |
| 4.98 | 17.72 | 54 |
| 5.69 | 15.52 | 8 |
| 6.32 | 13.97 | 34 |
| 6.48 | 13.63 | 35 |
| 7.12 | 12.41 | 12 |
| 7.49 | 11.80 | 11 |
| 8.08 | 10.93 | 4 |
| 8.49 | 10.41 | 6 |
| 8.96 | 9.86 | 7 |
| 9.50 | 9.31 | 5 |
| 10.19 | 8.68 | 5 |
| 10.80 | 8.18 | 8 |
| 11.16 | 7.92 | 18 |
| 11.88 | 7.44 | 7 |
| 12.51 | 7.07 | 7 |
| 12.79 | 6.92 | 11 |
| 13.17 | 6.72 | 7 |
| 13.68 | 6.47 | 7 |
| 14.36 | 6.16 | 10 |
| 14.98 | 5.91 | 13 |
| 15.51 | 5.71 | 14 |
| 15.70 | 5.64 | 12 |
| 16.21 | 5.46 | 8 |
| 17.09 | 5.18 | 10 |
| 17.48 | 5.07 | 9 |
| 18.10 | 4.90 | 9 |
| 19.18 | 4.62 | 11 |
| 19.43 | 4.56 | 13 |
| 19.95 | 4.45 | 11 |
| 20.89 | 4.25 | 11 |
| 21.29 | 4.17 | 10 |
| 22.19 | 4.00 | 9 |
| 23.07 | 3.85 | 10 |
| 23.76 | 3.74 | 9 |
| 24.43 | 3.64 | 8 |

In Table 1, the value "2Θ [°]" denotes the angle of diffraction in degrees and the value "d [Å]" denotes the lattice plane spacings determined in angstroms (Å).

According to the findings given in Table 1, the crystalline telmisartan sodium salt is characterized in that in the X-ray powder diagram it has the characteristic values d=20.95 Å, 17.72 Å, 13.97 Å, and 13.63 Å, inter alia.

The X-ray powder diagrams were recorded within the scope of the present invention using a Bruker D8 Advanced with an site-sensitive detector (SSD) ($CuK_\alpha$-radiation, = 1.5418 Å, 30 kV, 40 mA).

The crystalline sodium salt of telmisartan according to the invention may also be present in the form of the solvates and hydrates thereof, preferably in the form of the hydrates, most preferably in the form of the hemihydrate thereof.

In another aspect, the present invention relates to a method of producing the crystalline sodium salt of telmisartan according to the invention. The starting material used to prepare the crystalline sodium salt of telmisartan according to the invention may be the free acid of telmisartan, which may be obtained by methods known in the art (e.g., according to EP 502 314 A1).

To prepare the crystalline sodium salt according to the invention the free acid of telmisartan is taken up in a suitable solvent, preferably in an organic aprotic solvent, most preferably in an organic, aprotic and non-polar solvent. The solvents used according to the invention are most preferably toluene, chloroform, dichloromethane, tetrahydrofuran, diethyl ether, diisopropyl ether, methyl tert-butyl ether, acetone, methyl isobutyl ketone, benzene, or acetonitrile, of which toluene, benzene, and methyl isobutyl ketone are particularly preferred. Of outstanding importance according to the invention is toluene as solvent.

As a rule, between 0.5 mL and 5 mL, preferably between 1 mL and 3 mL, most preferably between 1.5 mL and 2.5 mL of the abovementioned solvent is used per gram of the free acid of telmisartan.

A suitable sodium salt is then added as a base to this solution or suspension. Suitable sodium salts within the scope of the present invention include sodium hydroxide, sodium hydride, sodium carbonate, sodium hydrogen carbonate, or sodium alkoxides. By sodium alkoxides are meant the sodium salts which are formed with lower alcohols, preferably with alcohols selected from among methanol, ethanol, isopropanol, n-propanol, tert-butanol, sec-butanol, isobutanol, n-butanol, and tert-amyl alcohol. Of particular interest according to the invention are sodium salts selected from among sodium hydroxide, sodium hydride, sodium ethoxide, and sodium methoxide; of these, sodium hydroxide and sodium methoxide are of particular importance according to the invention. The abovementioned sodium salts may be added to the reaction mixture as solids. However, in the case of sodium hydroxide this is preferably added in the form of aqueous solutions. It is particularly preferable to use concentrated aqueous solutions of sodium hydroxide. For example, sodium hydroxide solution may be used in a concentration of about 45 wt.-%.

The amount of sodium salt to be used naturally depends on the amount of free acid telmisartan used. According to the invention, at least 1 mol of sodium salt has to be added per mole of telmisartan. It is also possible according to the invention to add an excess of sodium salt. Preferably, 1 mol to 2.5 mol, more preferably 1 mol to 2 mol, most preferably 1 mol to 1.5 mol of sodium salt are added per mole of the acid telmisartan used.

If sodium hydroxide is used as the sodium salt and this is added in the form of an aqueous solution, according to a preferred embodiment of the process according to the invention, it may be helpful in some cases to add a water-miscible organic solvent. This is preferably selected from among methanol, ethanol, isopropanol, acetone, tetrahydrofuran, tert-butanol, 2-butanol, butanol, glycol, ethyl diglycol, 1,3-butanediol, 1,4-butanediol, tert-amyl alcohol, acetonitrile, nitromethane, formamide, dimethylformamide, N-methylpyrrolidinone, dimethylsulfoxide, dimethylacetamide, nitroethane, and methoxy-2-propanol, of which the abovementioned alcohols are particularly significant. It is particularly preferred, within the scope of the process according to the invention, to use methanol or ethanol, above all ethanol. Preferably, between 50 mL and 500 mL, more preferably between 100 mL and 400 mL, most preferably between 200 mL and 350 mL of this solvent are used per mol of telmisartan used, according to the invention.

Then the reaction mixture may be heated to speed up the progress of the reaction. Preferably, the reaction mixture is heated to a temperature of >40° C., most preferably to over 60° C., with thorough mixing. The maximum temperature which may be selected is naturally determined by the boiling temperature of the solvents used. If the solvents preferred according to the invention are used, the mixture is preferably heated to over 70° C. This heating is generally carried out for a period of from 15 minutes to 2 hours, preferably between 20 minutes and one hour. Then the solution obtained is filtered and any solid remaining in the filter is washed with one or more of the abovementioned solvents.

The filtrate obtained by the process described above is added slowly, preferably dropwise, to an organic solvent which is heated to a temperature of >40° C., preferably above 60° C., most preferably to boiling point. The solvent used is preferably an organic aprotic solvent, more preferably an organic, aprotic, and non-polar solvent. Solvents which may be used according to the invention are, most preferably, toluene, chloroform, dichloromethane, tetrahydrofuran, diethyl ether, diisopropyl ether, methyl tert-butyl ether, acetone, methyl isobutyl ketone, benzene, or acetonitrile, of which toluene, benzene, and methyl isobutyl ketone are particularly preferred. The solvent toluene is of exceptional importance according to the invention. At the same time as the filtrate is added to the heated solvent, in a preferred embodiment of the invention, some of the solvent is distilled off (optionally azeotropically). After all the filtrate has been added, more solvent (e.g., about one to two thirds of the total amount of solvent added by this stage) may optionally be removed by distillation.

The concentrated solution thus obtained is cooled, preferably to ambient (room) temperature, whereupon the telmisartan sodium salt crystallizes out. After crystallization is complete, the crystals are separated off, optionally washed with the organic solvent mentioned above and finally dried.

The crystalline telmisartan sodium salt according to the invention may also be obtained starting from the acid addition salts of formula 2

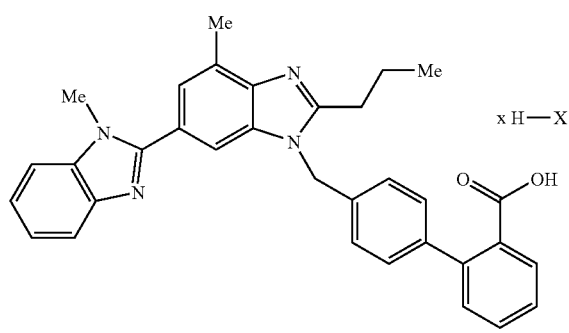

2 wherein H—X denotes an acid selected from among hydrochloric acid, hydrobromic acid, toluenesulfonic acid, or methanesulfonic acid. Of the abovementioned acid addition salts of formula 2, the salt wherein H—X denotes hydrochloric acid is of particular significance. This acid addition salt is also referred to hereinafter as telmisartan hydrochloride.

The compounds of formula 2 may be obtained, for example, from tert-butyl 4'-[[2-n-propyl-4-methyl-6-(1-methylbenzimidazol-2-yl)benzimidazol-1-yl]methyl]biphenyl-2-carboxylate (the tert-butyl ester of telmisartan) known from the prior art by saponification in acetic acid in the presence of the acid H—X.

In order to prepare the crystalline telmisartan sodium salt of formula 1 according to the invention starting from the acid addition salts of formula 2, the following procedure may be used, according to the invention.

The compound of formula 2 is taken up in a suitable solvent and combined with a suitable sodium salt. The solvent may be water and/or a suitable alcohol, such as methanol, ethanol, or isopropanol mixed with an aprotic organic solvent selected from among toluene, chloroform, dichloromethane, tetrahydrofuran, diethyl ether, diisopropyl ether, methyl tert-butyl ether, acetone, methyl isobutyl ketone, benzene, and acetonitrile. It is particularly preferred to use, as the solvent, water mixed with ethanol or isopropanol mixed with an aprotic organic solvent selected from among toluene, benzene, and methyl isobutyl ketone, most preferably toluene. A mixture of water, isopropanol, and toluene has proved particularly suitable for this step of the synthesis.

The amount of solvent or solvent mixture used depends on the amount of acid addition salt 2 used. Preferably, about 0.3 L to 3.5 L, preferably about 1 L to 2.5 L, more preferably about 1.5 L to 2 L of the abovementioned solvent or solvent mixture are used per mole of compound 2 used. If the solvent used is the preferred solvent mixture according to the invention which contains an alcohol as the third solvent component in addition to water and an aprotic organic solvent, the ratios by volume of water to aprotic organic solvent according to the invention are preferably in a range from 1:5 to 1:50 and the ratio of water to alcohol used is in a range from 2:1 to 1:40. Preferably, in a solvent mixture of this kind, the ratios of water to aprotic organic solvent are in the range from 1:10 to 1:30, preferably in the range from 1:15 to 1:25, and the ratio of water to alcohol used is in a range from 1:1 to 1:20, preferably in the range from 1:5 to 1:15.

Preferably, the solvent or solvent mixture mentioned above contains about 10 mL to 100 mL of water, preferably about 30 mL to 80 mL of water, most preferably about 40 mL to 70 mL of water, per mole of 2. Preferably the solvent or solvent mixture used also contains about 100 mL to 1000 mL of alcohol, preferably about 300 mL to 800 mL alcohol, most preferably about 400 mL to 700 mL alcohol, per mole of 2. Finally, the solvent or solvent mixture used preferably contains as the third component of the solvent, about 200 mL to 2000 mL of the abovementioned aprotic organic solvent, preferably about 600 mL to 1600 mL, most preferably about 800 mL to 1400 mL of the abovementioned aprotic organic solvent, per mole of 2.

Suitable sodium salts which may be used for reacting 2 to 1 include sodium hydroxide, sodium hydride, sodium carbonate, sodium hydrogen carbonate, or sodium alkoxides. By sodium alkoxides are meant the sodium salts which are formed with lower alcohols, preferably with alcohols selected from among methanol, ethanol, isopropanol, n-propanol, tert-butanol, sec-butanol, isobutanol, n-butanol and tert-amyl alcohol. Of particular interest according to the invention are sodium salts selected from among sodium hydroxide, sodium hydride, sodium ethoxide, and sodium methoxide, while the sodium alkoxides sodium ethoxide and sodium methoxide, particularly sodium methoxide, are of particular importance according to the invention for this reaction step. The abovementioned sodium salts may be added to the reaction mixture as solids. In the case of sodium methoxide, however, it is preferable to add it in the form of a methanolic solution. Methanolic solutions of sodium methoxide which contain it in a concentration of at least 10%, most preferably about 20% to 40% (w/w), are particularly preferred. For example, the methanolic sodium methoxide solution used may have a concentration of about 30 wt. %.

The amount of sodium salt to be used is naturally dependent on the amount of free acid telmisartan used. According to the invention, at least 2 mol of sodium salt have to be added per mole of telmisartan acid addition salt of formula 2 used. According to the invention it is also possible to add an excess of sodium salt.

It may be useful in some cases to add activated charcoal to the abovementioned reaction mixture. For example, it may be added in an amount of about 5 g to 50 g per mole of 2 used, preferably in an amount of about 10 g to 40 g per mole of 2 used.

After the sodium salt and optionally the activated charcoal has been added the reaction mixture obtained is heated to a temperature of about 50° C. to 100° C., preferably about 60° C. to 90° C., most preferably about 70° C. to 80° C. for a period of about 10 minutes to 2 hours, preferably for about 20 to 45 minutes. In the course of this heating, some of the solvent, preferably about 10% to 50%, most preferably about 20% to 40% of the total quantity of solvent may be distilled off.

The remaining suspension is then filtered, the filter residue is optionally washed with one of the abovementioned aprotic organic solvents, preferably with the aprotic organic solvent which is also used in the reaction.

The filtrate obtained is then diluted with a solvent or mixture of solvents. It is preferable to use a mixture of water and the abovementioned aprotic organic solvent for this. Preferably, at this point, about 10 mL to 100 mL of water, preferably about 30 mL to 80 mL of water, most preferably about 40 mL to 70 mL of water is used per mole of the compound 2 originally used. At this point, 250 mL to 3000 mL, preferably about 800 mL to 2000 mL, most preferably about 1200 mL to 1800 mL of aprotic organic solvent is used per mole of the compound 2 originally used.

After dilution, the mixture obtained is refluxed. Then about 1 L to 2 L, preferably about 1200 mL to 1800 mL of solvent are distilled off per mole of the compound 2 originally used. After the solvent has been distilled off, the telmisartan sodium salt 1 according to the invention crystallizes out. The crystals obtained are isolated, optionally washed with one of the abovementioned aprotic organic solvents, and finally dried.

Crystalline telmisartan sodium salt may also be obtained by the methods described above in the form of the solvates or hydrates thereof, preferably in the form of the hydrates thereof, most preferably in the form of the hemihydrate.

In view of the pharmaceutical activity of the crystalline telmisartan sodium salt according to the invention, it is used for preparing a pharmaceutical composition, particularly for preparing a pharmaceutical composition for the prevention or treatment of diseases wherein the administration of therapeutically effective doses of one or more angiotensin II antagonists may provide a therapeutic benefit. Preferably, the present invention relates to the use of crystalline telmisartan sodium salt for preparing a pharmaceutical composition for the prevention or treatment of diseases selected from among hypertension, cardiac insufficiency, ischemic peripheral circulatory disorders, myocardial ischaemia (angina), myocardial infarct, the progression of cardiac insufficiency after myocardial infarct, the prevention of cardiovascular deaths, stroke, diabetic neuropathy, diabetic nephropathy, diabetic retinopathy, glaucoma, gastrointestinal diseases, and bladder diseases, the prevention or treatment of hypertension, cardiac insufficiency, myocardial infarct, and stroke, and the prevention of cardiovascular deaths being particularly preferred.

Accordingly, the present invention is directed to a pharmaceutical composition characterized in that it contains telmisartan sodium salt optionally combined with other active substances such as diuretics.

For this purpose the active substance or substances are generally formulated with one or more excipients such as mannitol, sorbitol, xylitol, saccharose, calcium carbonate, calcium phosphate, lactose, croscarmellose sodium salt (cellulose carboxymethylether sodium salt, cross-linked), crospovidone, sodium starch glycolate, hydroxypropylcellulose (low-substituted), maize starch, polyvinylpyrrolidone, copolymers of vinylpyrrolidone with other vinyl derivatives (copovidone), hydroxypropylcellulose, hydroxypropylmethylcellulose, microcrystalline cellulose or starch, magnesium stearate, sodium stearylfumarate, talc, hydroxypropylmethylcellulose, carboxymethylcellulose, cellulose acetate phthalate, polyvinyl acetate, water, water/ethanol, water/glycerol, water/sorbitol, water/polyethylene glycol, propylene glycol, cetyl stearyl alcohol, carboxymethylcellulose, or fatty substances such as hard fat or suitable mixtures thereof, into conventional galenic preparations such as plain or coated tablets, capsules, powders, suspensions, or suppositories.

In a pharmaceutical composition containing the telmisartan sodium salt as the sole active substance, one or more excipients such as sorbitol, xylitol, saccharose, croscarmellose sodium salt, crospovidone, sodium starch glycolate, hydroxypropylcellulose, polyvinylpyrrolidone, copolymers of vinylpyrrolidone with other vinyl derivatives (copovidone), hydroxypropylcellulose, hydroxypropylmethylcellulose, microcrystalline cellulose or sodium stearylfumarate, hydroxypropylmethylcellulose, water, water/ethanol, water/glycerol, water/sorbitol, water/polyethylene glycol, propylene glycol, cetyl stearyl alcohol, carboxymethylcellulose, or fatty substances such as hard fat or suitable mixtures thereof may be used, in particular. Corresponding tablets may be obtained, for example, by mixing the active substance or substances with one or more excipients and subsequently compressing them. Examples of excipients are inert diluents such as mannitol, sorbitol, xylitol, saccharose, calcium carbonate, calcium phosphate, and lactose;

disintegrants such as croscarmellose sodium salt (cellulose carboxymethylether sodium salt, cross-linked), crospovidone, sodium starch glycolate, hydroxypropylcellulose (low-substituted), and maize starch;

binders such as polyvinylpyrrolidone, copolymers of vinylpyrrolidone with other vinyl derivatives (copovidone), hydroxypropylcellulose, hydroxypropylmethylcellulose, microcrystalline cellulose, or starch;

lubricants such as magnesium stearate, sodium stearyl fumarate, and talc;

agents for achieving delayed release such as hydroxypropylmethylcellulose, carboxymethylcellulose, cellulose acetate phthalate, and polyvinyl acetate; and pharmaceutically permitted colorings such as colored iron oxides.

The tablets may also consist of several layers.

The properties of tablets may sometimes also be influenced by granulating individual components and active substances before they are compressed and only then compressing them with other excipients.

Particularly suitable excipients for the direct compression of the telmisartan sodium salt as the active substance on its own or together with the diuretic hydrochlorothiazide are sorbitol and magnesium stearate, while these excipients may optionally be replaced by other excipients suitable for direct tabletting such as mannitol or saccharose. In order to differentiate visually between tablets with different compositions of active substances, it is useful to make these tablets in different colors. For this purpose, coloring excipients such as colored iron oxides or other pharmaceutically permitted colorings may be added before the compression process.

Particularly good solubility characteristics of the active substances are obtained in tablets which have been prepared by granulating the telmisartan sodium salt in a dry granulation process before the compression to form tablets. The salt is mixed, for example, with mannitol, hydroxypropylcellulose, and optionally a coloring excipient such as red iron oxide in suitable mixers, then screened and finally subjected to dry granulation in a roller compactor, for example. The excipients mentioned may be replaced, for example, by excipients such as lactose or microcrystalline cellulose. The granules obtained are then optionally mixed with another active substance such as hydrochlorothiazide as well as with excipients such as mannitol, microcrystalline cellulose, sodium starch glycolate, magnesium stearate, and optionally a coloring excipient, such as red iron oxide, in a suitable mixer and finally pressed into tablets. Alternatively, excipients such as lactose or croscarmellose sodium salt (cellulose carboxymethylether sodium salt, cross-linked) may also be used.

The content of telmisartan sodium salt is usually 60 mg to 90 mg, 30 mg to 60 mg, or 15 mg to 30 mg of the salt per tablet, coated tablet, or capsule. Amounts of 80 mg to 85 mg, 40 mg to 45 mg or 20 mg to 25 mg are preferred. These amounts correspond roughly to a content of 80 mg, 40 mg, and 20 mg, respectively, of the free acid telmisartan. If these formulations also contain hydrochlorothiazide, it is present in each tablet, coated tablet, or capsule in an amount of 10 mg to 15 mg or 20 mg to 30 mg, preferably 12 mg to 13 mg or 24 mg to 26 mg. Processes for preparing the abovementioned pharmaceutical compositions, particularly those wherein the active substances are compressed into tablets, are also a subject of the present invention.

Pharmaceutical active substances which may optionally be incorporated into formulations together with the telmisartan sodium salt are diuretics such as hydrochlorothiazide;
antihypertensives such as
ACE inhibitors (e.g., captopril, enalapril, lisinopril, ramipril, and perindopril);
angiotensin receptor antagonists (e.g., candesartan, eprosartan, irbesartan, losartan, telmisartan, and valsartan);
calcium antagonists (e.g., nifedipin and verapamil); or
alpha- or beta-receptor blockers (e.g., ergotamine, dihydroergotamine, atenolol, acebutolol, metoprolol, propranolol, and pindolol);
antidiabetics such as nateglinide, repaglinide, and metformin;
thrombocyte aggregation inhibitors such as clopidogrel, acetylsalicylic acid, or dipyridamole;
vasodilators such as minoxidil; and
lipid or cholesterol lowering agents such as procubol, sitosterol, MTP inhibitors, HMG-CoA-reductase inhibitors such as lovastatin, simvastatin, and atorvastatin, or fibrates.

The example of synthesis that follows serves to illustrate a method of preparing crystalline telmisartan sodium salt carried out by way of example. It is intended solely as a possible procedure provided by way of example, without restricting the invention to its contents.

Synthesis Example 1

Preparation of Crystalline Telmisartan Sodium Salt Starting from Telmisartan

The starting material used to prepare crystalline telmisartan sodium salt according to the invention may be the free acid, which may be obtained by methods known from the prior art (e.g., according to EP 502314 A1).

154.4 g of telmisartan is placed in 308.8 mL of toluene in a suitable reaction vessel. The suspension is combined with 27.8 g of 44.68% sodium hydroxide solution and 84.9 mL of ethanol and heated to 78° C. for about 30 minutes, then the mixture is filtered. If desired, if large amounts of solid are left in the filter, this may be washed with a mixture of 61.8 mL of toluene and 15.3 mL of ethanol.

463.2 mL of toluene is placed in another reaction vessel and refluxed. The filtrate obtained by the process described above is slowly added dropwise thereto at boiling temperature and simultaneously distilled off azeotropically. After it has all been added, any solution which may have been obtained from washing the filter is also added and again distilled off azeotropically. The mixture is distilled at up to 103° C. and the suspension is allowed to cool to ambient temperature. The crystals are suction filtered, washed with 154.4 mL of toluene and dried at 60° C. in the circulating air drier. Yield: 154.6 g (96%) of colorless crystals; $C_{33}H_{29}N_4O_2Na.0.5H_2O$; calc.: C, (72.51); H, (5.72); N, (10.25). found: C, (72.57); H, (5.69); N, (10.21).

Synthesis Example 2

Preparation of Crystalline Telmisartan Sodium Salt Starting from Telmisartan Hydrochloride A. Preparation of Telmisartan Hydrochloride 411 g of tert-butyl 4'-[[2-n-propyl-4-methyl-6-(1-methyl-benzimidazol-2-yl)benzimidazol-1-yl]methyl]biphenyl-2-carboxylate is suspended in 822 mL of glacial acetic acid and combined with 213 g of concentrated aqueous hydrochloric acid (37%). The mixture is refluxed and about 640 mL of solvent is distilled off. The residue remaining is slowly combined with about 620 mL of water at 50° C. to 60° C. To this mixture is added 20 g of activated charcoal (e.g., Norit SX 2 Ultra) and the resulting mixture is stirred for about 10 minutes at constant temperature. After filtering, the residue is washed three times with 25 mL of glacial acetic acid and about 620 mL of water. The filtrate obtained is again heated to about 50° C. to 60° C. and about 2 L of water are added. After stirring for about 12 hours at about 23° C., the crystals formed are suction filtered and washed twice with about 500 mL of water, once with about 900 mL of acetone, and then dried at about 60° C. Yield: 367 g (92.5%) colorless crystals, melting point: 278° C.

B. Preparation of Crystalline Telmisartan Sodium Salt from Telmisartan Hydrochloride 55.1 g of telmisartan hydrochloride is taken up in 110.2 mL of toluene, 5.5 mL of water, and 55.1 mL of isopropanol and this mixture is combined with 36.9 g of sodium methoxide (30% in methanol) and 2.75 g of activated charcoal (e.g., Sorit SX 2 Ultra). The mixture is then heated to about 75° C., and about 50 mL of solvent mixture is distilled off at constant temperature over about 30 minutes. The suspension obtained is filtered and the residue is washed with about 20 mL of toluene. The filtrate is combined with about 5 mL of water and about 150 mL of toluene. The mixture obtained is refluxed. During this time, about 150 mL of solvent mixture is azeotropically distilled off (at up to 102° C.). The mixture is left to crystallize for one hour at 100° C. The crystals are suction filtered, washed with about 50 mL of toluene, and dried at about 60° C. Yield: 53.6 g (99%) colorless crystals; $C_{33}H_{29}N_4O_2Na.0.5H_2O$; calc.: C, (72.51); H, (5.72); N, (10.25). found: C, (72.44); H, (5.68); N, (10.20).

To prepare a pharmaceutical composition containing the active substance, particularly an orally administered pharmaceutical composition, most preferably a tablet, procedures known in the art may be used.

Suitable tablets may be obtained, for example, by mixing the active substance(s) with known excipients, for example, inert diluents such as mannitol, sorbitol, xylitol, saccharose, calcium carbonate, calcium phosphate, or lactose, disintegrants such as croscarmellose sodium salt (cellulose carboxymethylether sodium salt, cross-linked), crospovidone, sodium starch glycolate, hydroxypropylcellulose (low-substituted), or maize starch, binders such as polyvinylpyrrolidone, copolymers of vinylpyrrolidone with other vinyl derivatives (copovidone), hydroxypropylcellulose, hydroxypropylmethylcellulose, microcrystalline cellulose, or starch, lubricants such as magnesium stearate, sodium stearyl fumarate, or talc and/or agents for obtaining delayed release, such as hydroxypropylmethylcellulose, carboxymethylcellulose, cellulose acetate phthalate, or polyvinyl acetate. The tablets may also comprise several layers.

The following are some examples of pharmaceutical preparations which may be used according to the invention. They are intended purely as illustrations by way of example without restricting the subject matter of the invention thereto.

Formulation Example 1

Tablet 1

| Ingredients | mg |
| --- | --- |
| Telmisartan sodium salt | 83.417 |
| Mannitol | 299.083 |
| Microcrystalline cellulose | 100.000 |
| Croscarmellose sodium salt | 10.000 |
| Magnesium stearate | 7.500 |
| Total | 500.000 |

Formulation Example 2

Tablet 2

| Ingredients | mg |
| --- | --- |
| Telmisartan sodium salt | 83.417 |
| Sorbitol | 384.083 |
| Polyvidone K25 | 25.000 |
| Magnesium stearate | 7.500 |
| Total | 500.000 |

Formulation Example 3

Tablet 3

| Ingredients | mg |
| --- | --- |
| Telmisartan sodium salt | 41.708 |
| Mannitol | 149.542 |
| Microcrystalline cellulose | 50.000 |
| Croscarmellose sodium salt | 5.000 |
| Magnesium stearate | 3.750 |
| Total | 250.000 |

Formulation Example 4

By directly compressing the telmisartan sodium salt with the excipients sorbitol and magnesium stearate tablets are obtained whose concentration of active substance corresponds to an amount of 80 mg, 40 mg, and 20 mg of free acid of telmisartan.

| Tablet Containing the Equivalent of 80 mg of Free Acid Telmisartan | | |
| --- | --- | --- |
| Ingredient | mg/Tablet | % Tablet |
| Telmisartan sodium salt | 83.417 | 17.379 |
| Sorbitol | 389.383 | 81.121 |
| Magnesium stearate | 7.200 | 1.500 |
| Total | 480.000 | 100.000 |

Shape: oval. Dimensions: 16.2×7.9 mm.

| Tablet Containing the Equivalent of 40 mg of Free Acid Telmisartan | | |
| --- | --- | --- |
| Ingredient | mg/Tablet | % Tablet |
| Telmisartan sodium salt | 41.708 | 17.378 |
| Sorbitol | 194.692 | 81.122 |
| Magnesium stearate | 3.600 | 1.500 |
| Total | 240.000 | 100.000 |

Shape: oval. Dimensions: 12×5.9 mm.

| Tablet Containing the Equivalent of 20 mg of Free Acid Telmisartan | | |
| --- | --- | --- |
| Ingredient | mg/Tablet | % Tablet |
| Telmisartan sodium salt | 20.854 | 17.378 |
| Sorbitol | 97.346 | 81.122 |
| Magnesium stearate | 1.800 | 1.500 |
| Total | 120.000 | 100.000 |

Shape: round. Dimensions: 7 mm.

Formulation Example 5

The telmisartan sodium salt is first mixed with mannitol, red iron oxide and hydroxypropylcellulose in an intensive mixer ("High-Shear Mixer"). Then magnesium stearate is added by sifting through a 0.8 mm screen and the mixture is subjected to dry granulation in a roller compactor. In parallel, hydrochlorothiazide is mixed with mannitol, microcrystalline cellulose, sodium glycol starch, and red iron oxide in an intensive mixer. Both this mixture and the granulated telmisartan sodium salt are sieved through a 0.8 mm screen, mixed together in a free fall blender, and finally subjected to a last mixing process with magnesium stearate screened through a 0.8 mm screen. A composition is obtained which can be compressed without any problems and the tablets produced from it exhibit good solubility for the active substances. This composition of active substances and excipients is compressed with a suitable tablet press (e.g., Korsch EK0 or Fette P1200). Tablets of the following composition are prepared, the amount of telmisartan sodium salt contained in each tablet corresponding to an amount of 80 mg of the free acid of telmisartan.

| Ingredient | mg/Tablet | % Tablet |
| --- | --- | --- |
| Telmisartan sodium salt | 83.417 | 13.903 |
| Hydrochlorothiazide | 12.500 | 2.083 |
| Mannitol | 336.483 | 56.081 |
| Cellulose microcrystalline | 120.000 | 20.000 |
| Sodium glycol starch | 30.000 | 5.000 |
| Red iron oxide | 0.600 | 0.100 |
| Hydroxypropylcellulose | 5.000 | 0.833 |
| Magnesium stearate | 12.000 | 2.000 |
| Total | 600.000 | 100.000 |

The composition of the tablet may also be as follows:

| Ingredient | mg/Tablet | %/Tablet | %/Granules |
| --- | --- | --- | --- |
| Telmisartan sodium salt | 83.417 | 13.903 | 83.417 |
| Mannitol | 10.983 | 1.831 | 10.983 |
| Hydroxypropylcellulose | 5.000 | 0.833 | 5.000 |
| Red iron oxide | 0.100 | 0.017 | 0.100 |
| Magnesium stearate | 0.500 | 0.083 | 0.500 |
| Total | 100.000 | 16.667 | 100.000 |
| Hydrochlorothiazide | 12.500 | 2.083 | |
| Mannitol | 325.500 | 54.250 | |
| Cellulose microcrystalline | 120.000 | 20.000 | |
| Sodium glycol starch | 30.000 | 5.000 | |
| Red iron oxide | 0.500 | 0.083 | |
| Magnesium stearate | 11.500 | 1.917 | |
| Total | 600.000 | 100.000 | |

The tablets have the following properties:
Dimensions: 16.2×7.9 mm (r=5.86 mm)
Weight: 598.7 mg±0.22%
Thickness: on average 6.16 mm
Breaking strength: on average 145 N
Abrasion: 0.09%
Decomposition time: on average 153 s 95±3.1% of the telmisartan sodium salt dissolve after 30 minutes in 900 mL of 0.1 M phosphate buffer, pH 7.5, with stirring (75 rpm). 88±3.8% hydrochlorothiazide dissolve after 30 minutes in 900 mL of 0.1 M HCl (100 rpm).

Formulation Example 6

Hydrochlorothiazide, telmisartan sodium salt, sorbitol, and red iron oxide are mixed in a free fall blender, passed through a 0.8 mm screen and, after the addition of magnesium stearate, processed in a free fall blender to form a powdered mixture.

This composition of active substances and excipients is then compressed into tablets using a suitable tablet press (e.g., Korsch EK0 or Fette P1200). Tablets of the following composition are prepared, the amount of telmisartan sodium salt contained in each tablet corresponding to an amount of 80 mg of the free acid of telmisartan.

| Ingredient | mg/Tablet | % |
| --- | --- | --- |
| Telmisartan sodium salt | 83.417 | 13.903 |
| Hydrochlorothiazide | 12.500 | 2.083 |
| Sorbitol | 494.483 | 82.414 |
| Red iron oxide | 0.600 | 0.100 |
| Magnesium stearate | 9.000 | 1.500 |
| Total | 600.000 | 100.000 |

The tablets of three batches have the following properties:
Batch 1:
Dimensions: 16.2×7.9 mm (r=5.86 mm)
Weight: 600.7 mg±0.34%
Thickness: on average 5.96 mm
Breaking strength: on average 142 N
Abrasion: 0.12%
Decomposition time: on average 304 s
Batch 2:
Dimensions: 16.2×7.9 mm (r=5.86 mm)
Weight: 600.6 mg±0.28%
Thickness: on average 6.11 mm
Breaking strength: on average 115 N
Abrasion: 0.17%
Decomposition time: on average 331 s
Batch 3:
Dimensions: 16.2×7.9 mm (r=5.86 mm)
Weight: 591.1 mg±0.56%
Thickness: on average 5.89 mm
Breaking strength: on average 116 N
Abrasion: 0.13%
Decomposition time: on average 416 s The telmisartan sodium salts of the tablets from the three batches dissolves after 30 minutes' stirring (75 rpm) in 900 mL of 0.1 M phosphate buffer pH 7.5 at 92±1.5%, 96±1.8% and 100±1.0%, respectively. The hydrochlorothiazide dissolved after 30 minutes in 900 mL of 0.1 M HCl (100 rpm) at 69±6.3%, 72±2.1% and 78±1.8%, respectively.

I claim:

1. A tablet or capsule comprising 30 to 90 mg of crystalline telmisartan sodium salt with a melting point of T=245° C.±5° C. and hydrochlorothiazide.

2. The tablet or capsule according to claim 1, further comprising one or more excipients selected from mannitol, sorbitol, xylitol, saccharose, calcium carbonate, calcium phosphate, lactose, croscarmellose sodium salt, crospovidone, sodium starch glycolate, hydroxypropylcellulose, maize starch, polyvinylpyrrolidone, copolymers of vinylpyrrolidone with other vinyl derivatives (copovidone), hydroxypropylcellulose, hydroxypropylmethylcellulose, microcrystalline cellulose or starch, magnesium stearate, sodium stearylfumarate, talc, hydroxypropylmethylcellulose, carboxymethylcellulose, cellulose acetate phthalate, polyvinyl acetate, water, water/ethanol, water/glycerol, water/sorbitol, water/polyethylene glycol, propylene glycol, cetyl stearyl alcohol, carboxymethylcellulose, and fatty substances, or suitable mixtures thereof.

3. The tablet or capsule according to claim 1, wherein the amount of the hydrochlorothiazide is 10 to 15 mg or 20 to 30 mg.

4. The tablet or capsule according to claim 3, wherein the amount of the hydrochlorothiazide is 12 to 13 mg or 24 to 26 mg.

5. A tablet or capsule comprising:
   (a) 30 to 90 mg of crystalline telmisartan sodium salt with a melting point of T=245° C.±5° C.;
   (b) hydrochlorothiazide; and
   (c) one or more excipients selected from sorbitol, xylitol, saccharose, croscarmellose sodium salt, crospovidone, sodium starch glycolate, hydroxypropylcellulose, polyvinylpyrrolidone, copolymers of vinylpyrrolidone with other vinyl derivatives (copovidone), hydroxypropylcellulose, hydroxypropylmethylcellulose, microcrystalline cellulose, sodium stearylfumarate, hydroxypropylmethylcellulose, water, water/ethanol, water/glycerol, water/sorbitol, water/polyethyleneglycol, propyleneglycol, cetyl stearyl alcohol, carboxymethylcellulose, and fatty substances, or suitable mixtures thereof.

6. The tablet or capsule according to claim 5, wherein the amount of the hydrochlorothiazide is 10 mg to 15 mg or 20 mg to 30 mg.

7. The tablet or capsule according to claim 6, wherein the amount of the hydrochlorothiazide is 12 mg to 13 mg or 24 mg to 26 mg.

8. The tablet or capsule according to one of claims 1, 2, 3, 4, 5, 6, and 7, wherein the amount of the crystalline telmisartan sodium salt is 60 mg to 90 mg.

9. The tablet or capsule according to claim 8, wherein the amount of the crystalline telmisartan sodium salt is 80 mg to 85 mg.

10. The tablet or capsule according to one of claims 1, 2, 3, 4, 5, 6, and 7, wherein the amount of the crystalline telmisartan sodium salt is 30 mg to 60 mg.

11. The tablet or capsule according to claim 10, wherein the amount of the crystalline telmisartan sodium salt is 40 mg to 45 mg.

12. A tablet or capsule comprising a crystalline telmisartan sodium salt with a melting point of T=245° C.±5° C., hydrochlorothiazide, sorbitol, and magnesium stearate, compressed directly into tablets.

13. A tablet or capsule comprising:

(a) compressed dry granules comprising 30 to 90 mg of crystalline telmisartan sodium salt with a melting point of T=245° C.±5° C., mannitol, magnesium stearate, and hydroxypropylcellulose; and (b) a mixture of hydrochlorothiazide, mannitol, microcrystalline cellulose, and sodium glycol starch.

14. A tablet or capsule comprising:

(a) 30 to 90 mg of crystalline telmisartan sodium salt with a melting point of T=245° C.±5° C.; and (b) one or more excipients selected from sorbitol, xylitol, saccharose, croscarmellose sodium salt, crospovidone, sodium starch glycolate, copolymers of vinylpyrrolidone with other vinyl derivatives (copovidone), hydroxypropylcellulose, hydroxypropylmethylcellulose, sodium stearylfumarate, hydroxypropylmethylcellulose, water, water/ethanol, water/glycerol, water/sorbitol, water/polyethyleneglycol, propyleneglycol, cetyl stearyl alcohol, carboxymethylcellulose, and fatty substances, or suitable mixtures thereof.

* * * * *